United States Patent
Lindenbaum

(10) Patent No.: US 7,841,806 B2
(45) Date of Patent: Nov. 30, 2010

(54) SOIL STABILIZATION SYSTEM

(75) Inventor: Leigh L. Lindenbaum, New York, NY (US)

(73) Assignee: TerraFusion, Inc., New York, NY (US)

( * ) Notice: Subject to any disclaimer, the term of this patent is extended or adjusted under 35 U.S.C. 154(b) by 0 days.

(21) Appl. No.: 12/097,345

(22) PCT Filed: Dec. 15, 2006

(86) PCT No.: PCT/US2006/048094
§ 371 (c)(1), (2), (4) Date: Jun. 13, 2008

(87) PCT Pub. No.: WO2007/070706
PCT Pub. Date: Jun. 21, 2007

(65) Prior Publication Data
US 2008/0298905 A1 Dec. 4, 2008

Related U.S. Application Data

(60) Provisional application No. 60/751,119, filed on Dec. 15, 2005.

(51) Int. Cl.
*E02D 3/00* (2006.01)
(52) U.S. Cl. .................................. 405/302.4; 405/15
(58) Field of Classification Search ............ 405/258.1, 405/302.4, 302.6, 284, 286, 15, 16, 17, 18, 405/19

See application file for complete search history.

(56) References Cited

U.S. PATENT DOCUMENTS

| 4,605,594 A | 8/1986 | Owens et al. |
| 5,397,392 A | 3/1995 | Derr |
| 5,820,302 A * | 10/1998 | Roberts et al. ............. 405/263 |
| 6,663,777 B2 * | 12/2003 | Schimel ..................... 210/603 |
| 6,699,709 B1 * | 3/2004 | Bonde et al. .................... 71/1 |
| 2003/0051522 A1 * | 3/2003 | Arnold et al. .................. 71/11 |
| 2003/0167529 A1 | 9/2003 | Landschutze |
| 2005/0176583 A1 * | 8/2005 | Stamets ....................... 504/100 |
| 2008/0245272 A1 | 10/2008 | Kucharski et al. |

FOREIGN PATENT DOCUMENTS

| CN | 1156775 | * | 8/1997 |
| CN | 1156775 A | | 8/1997 |
| EP | 0918045 A1 | | 5/1999 |
| WO | WO 2005/030942 A1 | | 4/2005 |
| WO | WO 2006/066326 A1 | | 6/2006 |

OTHER PUBLICATIONS

Whiffin, Victoria S., Microbial CaCo3 Precipitation for the Production of Biocement; School of Biological Sciences & Biotechnology; Murdoch University, Western Australia; Sep. 2004.

* cited by examiner

*Primary Examiner*—Frederick L Lagman
(74) *Attorney, Agent, or Firm*—The Eclipse Group LLP

(57) ABSTRACT

A construction article including a compacted mixture that includes soil and a crop plant biomass microorganism-expressed enzyme composition. A method of stabilizing soil including: (i) mixing together soil, water and a crop plant biomass microorganism-expressed enzyme composition to form a mixture; (ii) causing the mixture to be shaped into a selected structure; and (iii) causing the structure to be compacted.

31 Claims, 2 Drawing Sheets

100

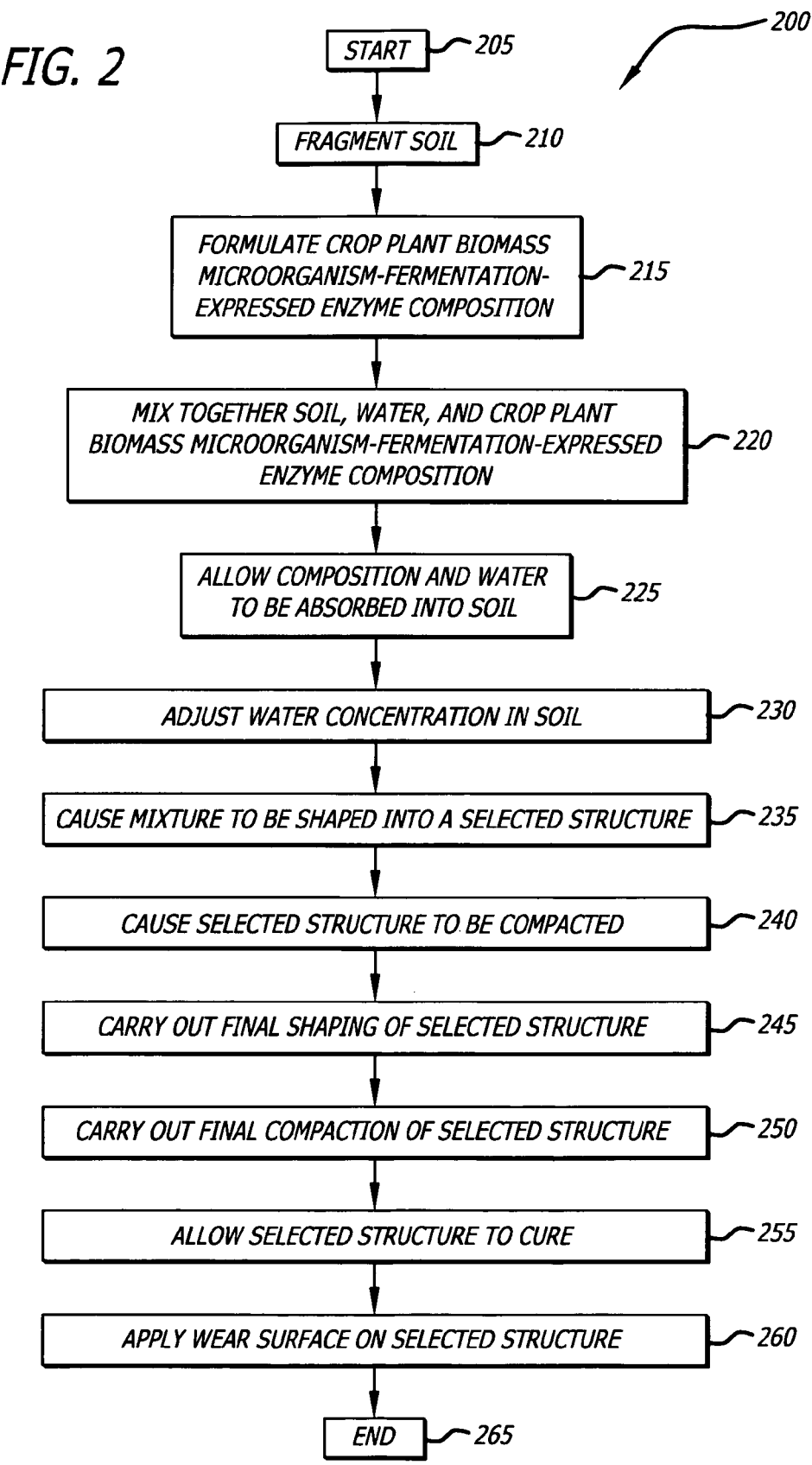

SOIL STABILIZATION SYSTEM

RELATED APPLICATIONS

This application claims priority to U.S. Provisional Patent Application Ser. No. 60/751,119, filed Dec. 15, 2005, titled SOIL STABILIZATION SYSTEM, which application is incorporated in its entirety by reference in this application.

BACKGROUND OF THE INVENTION

1. Technical Field

The invention relates to construction articles, including stabilized soil, and to methods for stabilizing soil.

2. Background Art

Dirt roads, dirt-excavated ponds, levees, railroad embankments, and other earthen structures have been in widespread use for eons. However, erosion and other breakdowns in such earthen structures both at the surface and from within have been perennial problems. High clay concentrations in soils can lead to expansion-contraction cycles, and low clay concentrations can prevent integration of a soil into a monolithic body capable of enduring water exposure and of withstanding its penetration. Clay materials strongly bind water with an accompanying expansion or swelling, making the soil difficult to dry. When clay materials are thoroughly dried, they contract as the water escapes. This expansion and contraction often results in general instability of the dimensions and solidity of soil materials. Air voids in soil create pathways for soil movement within earthen structures, adding to this instability. In many soil formations, such as road beds and pond beds, soil instability causes major construction problems. Water-containment structures such as lakes frequently accumulate leaks, causing loss of the contained water, degradation of the containment structures, and other problems caused by water escape. Friction among soil particles can require application of high pressures to compact the soil.

A continuing need exists for methods of stabilizing soil, and for solid, self-sustaining articles including soil.

DISCLOSURE OF INVENTION

In an example of an implementation, a construction article is provided, including a compacted mixture including soil and a crop plant biomass microorganism-expressed enzyme composition. As examples, the construction article may be shaped as a brick, block, board, tile, or paver. In a further example, the enzyme composition may include a ureolytic enzyme. The mixture may, as another example, include a nitrate ion source.

As another example of an implementation, a method of stabilizing soil is provided, including: mixing together soil, water and a crop plant biomass microorganism-expressed enzyme composition to form a mixture; causing the mixture to be shaped into a selected structure; and causing the structure to be compacted. In examples, the method may include mixing together soil, water and a crop plant biomass microorganism-expressed enzyme composition that includes a ureolytic enzyme, or such a composition that includes an enzyme expressed by a ureolytic microorganism. As a further example, the method may include mixing together soil, water, a crop plant biomass microorganism-expressed enzyme composition, and a nitrate ion source. Causing such a mixture to be shaped into a selected structure may include, in additional examples, forming an article such as a brick, block, board, tile, or paver.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF DRAWINGS

The components in the figures are not necessarily to scale, emphasis instead being placed upon illustrating the principles of the invention. In the figures, like reference numerals designate corresponding parts throughout the different views.

FIG. 2 is a flow chart showing an example of an implementation of a method 200 of stabilizing soil.

MODES FOR CARRYING OUT THE INVENTION

Figure 1:
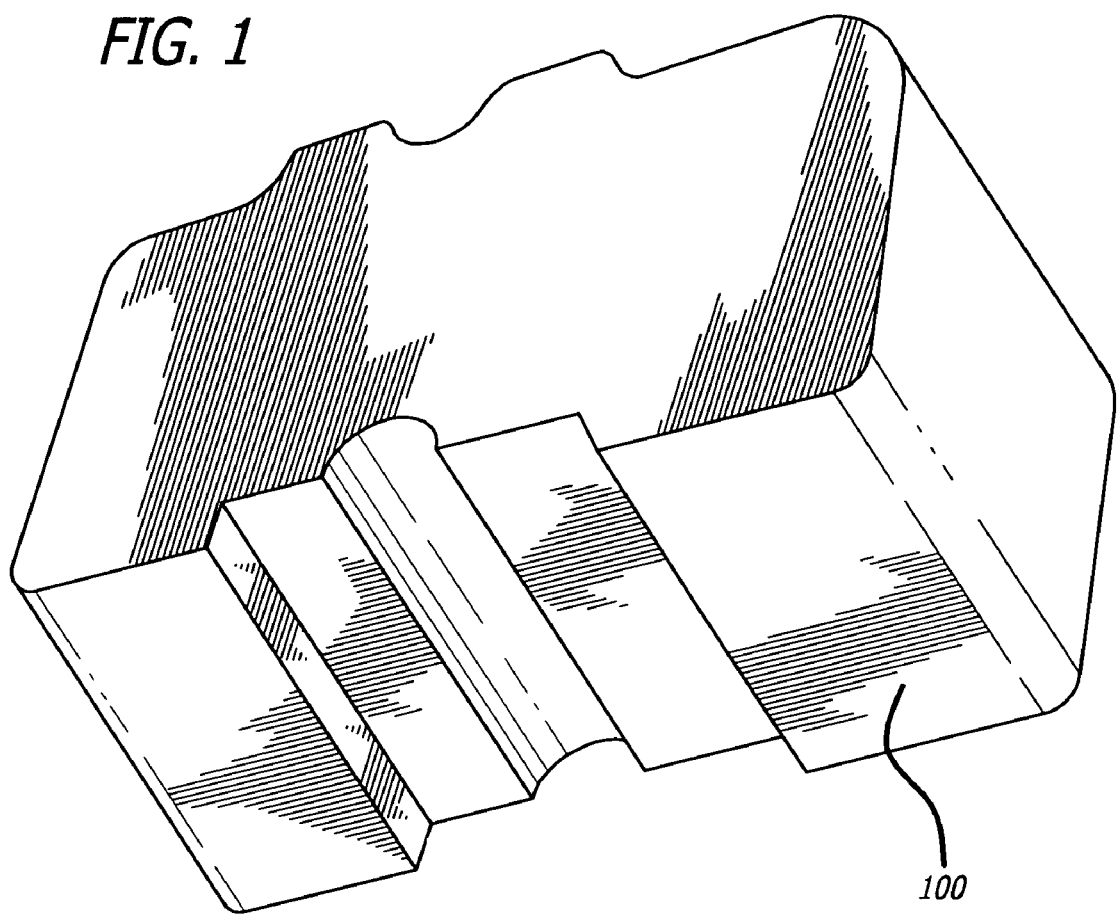
FIG. 1 is a photograph showing a perspective view of an example of an implementation of a construction article 100.

A construction article is provided, including a compacted mixture including soil and a crop plant biomass microorganism-expressed enzyme composition. As examples, the construction article may be shaped as a brick, block, board, tile, or paver. In a further example, the enzyme composition may include a ureolytic enzyme. The mixture may, as another example, include a nitrate ion source. Further, a method of stabilizing soil is provided, including: (i) mixing together soil, water and a crop plant biomass microorganism-expressed enzyme composition to form a mixture; (ii) causing the mixture to be shaped into a selected structure; and (iii) causing the structure to be compacted. In examples, the method may include mixing together soil, water and a crop plant biomass microorganism-expressed enzyme composition that includes a ureolytic enzyme, or such a composition that includes an enzyme expressed by a ureolytic microorganism. As a further example, the method may include mixing together soil, water, a crop plant biomass microorganism-expressed enzyme composition, and a nitrate ion source.

Soils include chemical substances that may react with other chemicals if certain conditions are present. These reactions may, for example, result from attraction between positive and negative charges in components of the soil and the chemical substances. Alterations in these charges consequently may change properties of the soil materials.

Absorbed water in soil may adhere to the entire surface of an individual soil particle. This film of water enveloping the soil particle, which may ultimately govern the expansion and shrinkage of colloidal soil constituents, may not be completely removable by purely mechanical methods. However, by means of temperature changes and addition or removal of water with mechanical pressure, it may be possible to vary the amount of water held by soil in this manner. Such variations are attended by swelling or shrinkage.

Subgrade soil materials, aggregates and mixtures of crushed rock with soils may behave as electrolyte systems, such that ion exchanges may occur within the materials. Knowledge of layered lattice structures that may be present in clay materials, and of colloid transport and osmotic pressure gradients, may be important in understanding the behavior of these electrolytic soils. Clays may have a molecular structure with an anionic, net negative charge. To maintain electrical neutrality, positively charged cations may be attracted to and held onto edges and surfaces of clay particles. These cations are called "exchangeable cations" because cations of one type may often be exchanged with cations of another type. When a cation charge in a clay structure is weak, the remaining negative charge that is not neutralized by the weak cations may attract polarized water molecules, filling the spaces of the clay structure with ionized water.

Individual cations may be unable to disperse freely through the soil structure because of their attraction to the negatively charged surfaces of clay particles. This inability to disperse evenly throughout the soil structure may create an osmotic pressure gradient in favor of equalization of the cation concentration.

A movement of water molecules from areas of low cation concentration to areas of high cation concentration may be catalyzed to approach equilibrium of the cation concentration throughout the soil.

Colloids are amorphous particles without crystalline structure having an average diameter of less than about a micron. Particles of this size are influenced by Brownian motion caused by random thermal gradients. Colloids may be present in a high concentration in a soil including clay. Colloids may have a net negative charge that enables them to attract and transport free cations in the soil as an electrolyte solution. Colloids may subsequently lose the cations upon passing close to a more strongly anionic clay particle, leaving the colloids free to then attract further free cations.

Both electrochemical and physical effects may have influence in this transport mechanism. The physical phenomena may be related to Brownian motion, laminar shear velocity and pore size distribution. Brownian motion may overcome effects of gravitational force and prevent deposition of free cations. Laminar shear velocity may affect a rate of cation exchange with the clay structure. The pore size distribution may determine a shear velocity and a proximity of a clay lattice to passing colloids and cations.

The electrochemical effects may be related to attractive Van der Waals forces between positive and negative particles, and to repulsion forces between multiple ions having the same charge.

If a solution including cations is introduced into a clay structure, a microenvironment may be generated in which the cations may be prevented from dispersing by the adjacent repulsive cations in the clay lattice. If the soil is not completely saturated with water, the liquid phase may be moved in a laminar flow through voids in the soil by capillary forces, leaving a higher concentration of cations close to the soil surface.

These capillary forces may generate an osmotic pressure gradient, which may draw colloidal particles from zones of lower cation concentration to zones of higher cation concentration. These colloidal particles may take up some of the free cations, reducing the ion concentration and the osmotic gradient pressure. This uptake may result in a hydraulic gradient pressure in the opposite direction, which may take cation-transporting colloids outward from a zone of high cation concentration to generate another zone of high cation concentration where a clay lattice is present, resulting in a new zone of osmotic pressure and high cation concentration.

The flow of cations through clay deposits in soil provides shrinking and swelling properties in soil. When a cationic material is added into the soil, the magnitude of neutralization of osmotic pressure gradients may depend on the valence and size of the cation. The cation size may determine mobility of the cation. Smaller cations may travel a greater distance throughout the soil structure than larger cations. The hydrogen ion is the smallest cation. Regarding valence, the hydrogen ion may be doubly effective in affecting the clay structure because even though it has only a single valence charge, the hydrogen ion produces an effect equivalent to a valence of two due to its high ionization energy. Hydrogen cations may be generated in soil in an acidic environment. Hydrogen cations may exert a strong pull on the clay lattice, bringing the structure of the soil together and removing trapped water that may be attracted to clay particles in between sodium and potassium cations. A loss of bound water results in a strengthening of the molecular structure of the clay and also in a reduction of the clay particle size and plasticity. A change in the environment of the clay in a soil from a basic to acidic state may result in a persistent change of the molecular structure of the soil.

Organic cations generated by the growth of vegetation may have the capacity to exchange with other cations in the clay lattice. Some organic cations so generated may be huge in size, equaling the size of smaller ones of the clay particles. These large organic cations may blanket an entire clay particle, neutralizing its negative charges and thus reducing its sensitivity to moisture.

The electrostatic characteristics of soil particles are factors in soil-enzyme interactions. In an example, enzymes may lower the dipole moments of water molecules and dissociation may then occur to form a hydroxyl (−) ion and a hydrogen (+) ion. The hydroxyl ion in turn may dissociate into oxygen and hydrogen, and the hydrogen atom of the hydroxyl ion may be transformed into a hydronium ion. The hydronium ion can accept or reject either positive or negative charges, depending on the circumstances. The finest colloidal particles of soil may be negatively charged. The enveloping film of absorbed water around soil particles may, as an example, contain a sufficient number of positive charged metal ions— such as sodium, potassium, aluminum and magnesium—to ensure charge equalization with respect to the electrically negative soil ion. Positively charged hydronium ions cr negatively charged hydroxyl ions may combine with positively charged metal ions in the water adhering to the surface of the particles.

Because of the effect of an enzyme in reducing the electric charges of water molecules, there may be sufficient negative charges to exert adequate pressure on the positively charged metal ions to remove them from the absorbed water film. When this existing electrostatic potential barrier is broken, the metal ions may migrate freely into the unbound water, and may then be removed from the soil by washing them out to the soil surface and evaporating the water. Thus, the film of absorbed water enveloping the clay particles may be reduced. The clay particles may thereby lose their swelling capacity and the soil as a whole may acquire a friable structure. The hydrogen ions, which are liberated in the dissociation of the water molecules, may once again react with free hydroxyl ions and form water along with gaseous hydrogen.

After the absorbed water content, of the soil is reduced, the soil particles may tend to agglomerate. As a result of the resulting relative movement between particles, the surface area may be reduced and less absorbed water may be held, which in turn may reduce the swelling capacity of the soil.

As an example, crop plant biomass microorganism-expressed enzyme compositions may be adsorbed by the clay lattice in soil, and then released upon a complete cycle of exchange with metal cations such as sodium and potassium. Crop plant biomass microorganism-expressed enzyme compositions may initially cause the clay lattice to expand and then to tighten. Crop plant biomass microorganism-expressed enzyme compositions may also be absorbed by colloids, enabling enzyme molecules to be transported through soil electrolyte media. Crop plant biomass microorganism-expressed enzyme compositions may also may help soil bacteria to release hydrogen ions, resulting in an acidic pH gradient at the surfaces of clay particles, which may assist in breaking up the structure of the clay and facilitating its compaction.

Crop plant biomass microorganism-expressed enzyme compositions may combine with large organic molecules in the soil to form a reactant intermediary, which then may exchange ions with the clay structure. This ion exchange may break down the clay lattice and cause clay particles to be blanketed according to the "cover-up effect", which prevents further absorption of water and resultant loss of soil density. The crop plant biomass microorganism-expressed enzymes are then regenerated as the reactant intermediaries complete a reaction cycle by disassociating from the clay lattice, and may then react with it again. Because the reactant intermediary ions are large, little osmotic migration takes place in them, and a good mixing process may be utilized.

When the crop plant biomass microorganism-expressed enzyme compositions are added to a soil, the enzymes may, for example, increase the wetting and bonding capacity of the soil particles. These crop plant biomass microorganism-expressed enzymes may allow soil materials to become more easily wet and more densely compacted. These crop plant biomass microorganism -expressed enzymes may also improve chemical bonding to fuse the soil particles together, creating a more permanent structure that is more resistant to weathering, wear and water penetration.

The crop plant biomass microorganism-expressed enzyme compositions may increase wetting of soil particles, allowing higher compaction of soil. The crop plant biomass microorganism-expressed enzyme compositions may cement soil by forming weak ionic bonds between negative and positive ions present in the soil structure. The crop plant biomass microorganism-expressed enzyme compositions may accelerate cohesive bonding of soil particles and create a tight permanent layer.

The stabilized soil may have increased compressive strength, as the crop plant biomass microorganism-expressed enzyme composition may act as a catalyst to accelerate and strengthen soil bonding. The enzymes may result in a denser, more cohesive and stable soil. The stabilized soil may need less compaction effort and may have improved soil workability. The enzymes may enable water to lubricate soil particles, helping them slide into a densest position. The wetting action of the crop plant biomass microorganism-expressed enzyme composition may enhance this sliding action during compaction making the soil easier to grade and allowing a compactor to achieve a targeted soil density with fewer passes. Water and the crop plant biomass microorganism-expressed enzyme composition may also assist in bonding together of clay particles.

The stabilized soil may have increased density and be tighter and drier, as voids between soil particles may be reduced by altering electrochemical attraction in soil particles and releasing bound water. The stabilized soil may have lowered water permeability and resultant greater resistance to deterioration caused by water penetration, as a tighter soil configuration reduces the migration of water that otherwise may occur in voids between particles.

As an example, macromolecules in a crop plant biomass microorganism-expressed enzyme composition may provide a surfactant-like action that aids in the dispersion of soil particles and provides cementation effects in the soil. When mixed with water and applied prior to soil compaction, the crop plant biomass microorganism-expressed enzyme composition may act upon organic fines contained in the soil through a catalytic bonding process, producing a strong cementation action. As an example, a crop plant biomass microorganism-expressed enzyme composition may lower the surface tension of water, which may promote fast and thorough penetration of the composition into soil, as well as dispersal of moisture from the soil. This penetrative action may, as an example, cause hydrated clay particles to be pressed into and to fill voids throughout the soil, thus forming a tight, dense, permanent stratum. A resulting increased lubricity of soil particles may allow a designated soil density increase to be reached with less compaction force.

Soils with too high or too low a moisture content may, for example, inhibit penetration of a crop plant biomass microorganism-expressed enzyme composition into the soil. In a given soil sample there is a proportional amount of water that may be determined, called the optimum moisture content, at which it is possible to obtain a maximum compressed density with a given amount of compactive effort. A crop plant biomass microorganism-expressed enzyme composition may reduce, by about 25% as an example, the amount of water required to reach a desired optimum moisture level of the soil. A crop plant biomass microorganism-expressed enzyme composition may facilitate this reduced water addition by promoting rapid saturation and by inhibiting surface evaporation. The crop plant biomass microorganism-expressed enzyme composition may also provide cementation action that increases weight bearing characteristics of soil by promoting a closer binding of soil particles. This binding may reduce a tendency of the soil to expand after compaction and may result in a strong, stable earth layer. By achieving greater bonding density, soil materials may better resist migration of water.

FIG. 1 is a photograph illustrating a perspective view of an example of an implementation of a construction article 100. The construction article 100 includes a compacted mixture including soil and a crop plant biomass microorganism-expressed enzyme composition. FIG. 1 shows that the construction article 100 has a firm, self-sustaining structure and an appearance similar to that of a concrete block. As an example, the construction article 100 may, as shown in FIG. 1, be shaped as a brick. The brick shape may include projecting and recessed portions suited for assembling and bonding together a plurality of such construction articles 100 in a modular arrangement to collectively form a structure such as a wall. It is understood by those skilled in the art that the construction article 100 may take other shapes (not shown), such as a block, board, tile, or paver.

The construction article 100 includes a compacted mixture including a crop plant biomass microorganism-expressed enzyme composition. For example, such a composition may include an enzyme expressed by microorganisms in fermentation of a crop plant biomass. Such microorganisms may include, as examples, bacteria and fungi. In an example, ureolytic microorganisms may be selected. Urea is converted by certain microorganisms into ammonium carbonate, releasing ammonium cations that are then converted by certain microorganisms into nitrite ions and then into nitrate ions. Nitrate ions are taken up as a nutrient by certain plants. There are other sources of nitrate ions which are commonly added to soil. Ammonium nitrate, ammonium sulfate, ammonium carbonate and ammonium bicarbonate as examples, are direct sources of ammonium cations for in situ conversion into nitrate ions. Ammonium nitrate is additionally a direct source of nitrate ions. Ammonia, as another example, ionizes into ammonium ions. Fermentation may include incubation of selected microorganisms together with a crop plant biomass under conditions suitable for growth of the microorganisms. The selected microorganisms may then collectively express such an enzyme in a harvestable amount and concentration. Selected microorganisms may further express a plurality of enzymes. A crop plant biomass for fermentation may include, as examples, selected parts of one or a plurality of plants. A crop plant may include, for example, a type of plant selected and cultivated as a crop. As another example, a crop plant biomass may include all parts or selected parts of a crop plant. A crop plant may, for example, include one or a mixture of the following: cereals, vegetables, roots, tubers, fruits, oil crops, pulses, vegetable fibers, nuts, forestry products, and horticultural products.

As an example, an enzyme may be a biologically-produced proteineic substance having specific activation in which the enzyme combines with its substrate in a stereoscopic position such that the enzyme causes changes in the electronic configuration around certain susceptible molecular bonds, catalyzing some bond formation or breakage in the substrate. In another example, "catalyzing" may include causing a specific chemical reaction to proceed at an accelerated rate. In one example, the enzyme composition may include an enzyme expressed by ureolytic microorganisms. As a further example, the enzyme composition may include a ureolytic enzyme. In an additional example, the enzyme composition may include an active ureolytic enzyme, having ureolytic activity. Such an active ureolytic enzyme may convert urea that may be present in the crop plant biomass microorganism-expressed enzyme composition or in the soil, into cationic ammonium ions. In an example, the crop plant biomass microorganism-expressed enzyme composition may include a plurality of enzyme groupings. As another example, each of a plurality of enzyme groupings may have enzymatic activity catalyzing the same or different steps of the nitrogen cycle. According to the nitrogen cycle, for example, amine moieties in amino acids and in other nitrate ion sources may be successively converted into ammonium ions, nitrite ions, and nitrate ions. Nitrate ion sources including ammonium ions, nitrite ions, or nitrate ions may, for example, be included in a crop plant biomass microorganism-expressed enzyme composition. As an additional example, the enzyme composition may include an enzyme synthesized by a plant. Such a plant enzyme may remain enzymatically active in the enzyme composition.

As additional examples, the enzyme composition may include one or more of the following types of enzymes: urease, hydrolase, amidohydrolase, oxidoreductase, transferase, lyase, aspartase, 1-glutaminase, dehydrogenase, acid phosphatase, alkaline phosphatase, arylsulfatase, betaglucosidase, amylase, catalase, alkaline phosphomonoesterase, phosphodiesterase, deaminase, invertase, cellulase, protease, asparaginase, amidase, chitinase, lipase, carbohydrase, phenoloxidase, peroxidase, laccase, lipase, aminopeptidase, and glucose oxidase.

Further enzymes that may be utilized are disclosed in Zahir, Z. A., et al., "Soil Enzymes Research: A Review", OnLine Journal of Biological Sciences, Vol. 1, No. 5, pp. 299-307 (2001), the entirety of the article of which is incorporated into this application by reference. Termite and ant enzymes may, as examples, also be utilized.

The crop plant biomass microorganism-expressed enzyme composition may, for example, be edible. In a further example, the crop plant biomass microorganism-expressed enzyme composition may generally be non-harmful to fish, animals, other wildlife, vegetation, and watersheds. The crop plant biomass microorganism-expressed enzyme composition may, for example, be biodegradable.

The crop plant biomass microorganism-expressed enzyme composition may not irritate skin tissue and may not cause rashes or burns. The crop plant biomass microorganism-expressed enzyme composition may, for example, contain no combustible materials and may be non-explosive. The crop plant biomass microorganism-expressed enzyme composition may, as an example, be non-gaseous and may be suitable for storage in poorly ventilated areas.

The microorganisms utilized in fermenting the crop plant biomass may, for example, be substantially inactive in the crop plant biomass microorganism-expressed enzyme composition. As a further example, a pH of the crop plant biomass microorganism-expressed enzyme composition may be a substantially neutral pH within a range of between about 7 and about 8.

In an example, the construction article 100 may include a crop plant biomass microorganism-expressed enzyme composition that may include a nitrate ion source. As examples, nitrate ion sources include amino acids, urea, and compositions including ammonium, nitrite, or nitrate ions. Urea, for example, may be converted by the enzymes or by microorganisms in the soil into ammonium ions. A nitrate ion source may be added to the construction article 100, for example, in one or more of the following forms: ammonium ions ($NH_4^+$), nitrite ions ($NO_2^-$), nitrate ions ($NO_3^-$), and amines such as urea ($CON(H_2)_2$.

The construction article 100 includes a compacted mixture including soil. Soil may be utilized in the construction article 100 that includes cohesive colloidal fines able to pass a 200 mesh screen, at a concentration within a range of between about 8% by weight and about 30% by weight of the soil. Such a concentration may include sufficient fines for adequate soil cohesiveness while not having excessive potential for expansion and contraction. Such cohesive fines may include clays, which attract water molecules and may be characterized by high water retention as well as marked expansion and contraction dependent on uptake and loss of such water, or other fines characterized by high water retention. In further examples, a soil may be selected that includes cohesive colloidal fines passing a 200 mesh screen at a concentration within a range of between about 8% by weight and about 20% by weight of the soil, or between about 8% by weight and about 11% by weight of the soil, or between about 15% by weight and about 20% by weight of the soil. In further examples, a soil having a well-graded distribution of sizes of particles may be utilized. Such a soil may, as an example, be readily compacted into a dense construction article 100 as the various sizes of particles may collectively fill voids and fit tightly together.

In an example, the construction article 100 may include less that about 10% by weight of vegetation. Vegetation may include cellulosic materials, such as straw. As one example, the construction article 100 may be formed without being subjected to heat curing such as firing in a kiln at an elevated temperature. Utilizing a crop plant biomass microorganism-expressed enzyme composition may, as examples, increase the resilient modulus and shear strength of the construction article 100.

As illustrated, the construction article 100 is compacted. For example, the construction article may have a dense structure resulting from formation of the construction article 100 by compaction, under an elevated pressure, of a mixture including soil, water and a crop plant biomass microorganism-expressed enzyme composition. Compaction pressure in pounds per unit surface area may be utilized in forming a construction article 100 comparable to a compaction pressure in pounds per unit area generated by road construction equipment such as a drum roller, a sheeps foot roller, or a vibrating roller.

FIG. 2 is a flow chart showing an example of an implementation of a method 200 of stabilizing soil. In an example, the method 200 may include (i) mixing together soil, water and a crop plant biomass microorganism-expressed enzyme composition to form a mixture; (ii) causing the mixture to be shaped into a selected structure; and (iii) causing the structure to be compacted.

The method 200 begins at step 205 and at step 210, the soil to be stabilized may be fragmented. As examples, the soil to be stabilized may be soil utilized to form a road, parking lot or trail. The surface of such soil to be stabilized may be dense, dusty and hard when dry, even though the same surface may be soft and muddy when wet. Accordingly, to facilitate mixing the soil to be stabilized together with water and a crop plant biomass microorganism-expressed enzyme composition, breaking up such a dry, dense, hard surface may be carried out at step 210. For example, the soil to be stabilized may be scarified with road-working equipment suitable to scratch the soil surface to a selected depth. The scarified soil may then be subjected to further steps of the method 200. The hard soil surface below the scarified soil may be referred to as the subsurface. A selected scarification depth may be determined based on the intended type of usage for the stabilized soil surface. For example, the axle weight of vehicles expected to utilize a road may be utilized to determine the depth of soil that may need to be stabilized on a subsurface to bear such weight. It is understood that if a given stabilized soil depth is found insufficient to support the actual vehicular traffic through a selected life cycle for a road, then a greater stabilized soil depth may be selected.

At step 215, a crop plant biomass microorganism-expressed enzyme composition may be formulated at a selected concentration for mixing at step 220 with the soil to be stabilized. Such a crop plant biomass microorganism-expressed enzyme composition may be initially prepared as discussed above in connection with the construction article 100 shown in FIG. 1. As an example, such a crop plant biomass microorganism-expressed enzyme composition may include a concentrated solution of such an enzyme. A dilution factor for such a concentrated enzyme solution may be selected for efficient utilization of the enzymes. As an example, one gallon of a concentrated enzyme solution may be sufficient for mixing with about 1,000 gallons of water, for subsequently mixing with about 165 cubic yards of soil. In another example, 15 gallons of a concentrated enzyme solution may be sufficient for mixing with an amount of soil equivalent to a 25-foot wide roadway having a depth of 6 inches and a length of one mile. Concentrated enzyme solution may be added to a water tank for mixing after the water has been filled into the tank to prevent excessive foam generation.

At step 220, the soil to be stabilized, water, and a crop plant biomass microorganism -expressed enzyme composition are combined to form a mixture. In an example, a reasonable effort may be made before forming such a mixture to remove vegetation such as cellulosic materials including wood, mulch and leaves from the surface of the soil to be stabilized. For example, a concentration of cellulosic materials in the soil to be stabilized may be reduced to less than about 10% by weight. Where step 210 may be carried out to fragment the soil, removal of such cellulosic materials may be carried out before the fragmentation is done. A concentration of cohesive colloidal fines in the soil to be stabilized may further be determined and adjusted. To determine such a concentration, ASTM International Standard No. D422-63 (2002)e1, "Standard Test Method for Particle-Size Analysis of Soils" ("ASTM D422") may be utilized, as well as other testing methods. The ASTM D422 article is incorporated in its entirety in this application by reference. The concentration of cohesive colloidal fines in soil to be stabilized may be upwardly and downwardly adjusted by additions to the soil of fines or of fines-free soil, respectively. Suitable concentrations of cohesive fines may, as examples, be those within the same ranges as discussed above in connection with the construction article 100. As another example, a soil may be selected that includes cohesive colloidal fines passing a 200 mesh screen at a concentration in excess of about 95% by weight. Where a soil including cohesive colloidal fines passing a 200 mesh screen at a concentration of less than about 8% by weight is selected, such a concentration may as an example be increased by addition of "dirty fines" to the soil. Such "dirty fines" may generally include, for example, cohesive fines having particle sizes such that about 15% to about 20% by weight of the fines pass a 200-mesh screen.

Where the soil to be stabilized is a lake bed for example, step 220 may be carried out without removal of the lake water. Where a maximum depth of the lake water is no greater than about 8 feet for example, lake water removal may not be needed. To carry out step 220, about 1 gallon of concentrated crop plant biomass microorganism-expressed enzyme composition may be applied to the lake bed per 6,000 square feet of lake surface area. In application, the concentrated crop plant biomass microorganism-expressed enzyme composition may be poured into the lake from the windward side and around the perimeter, or distributed evenly across the lake from a boat. The concentrated crop plant biomass microorganism-expressed enzyme composition may then form a mixture with the lake bed soil subsurface. Following addition of the concentrated crop plant biomass microorganism-expressed enzyme composition, further water entry into the lake may be prevented for a curing period. For example, the curing period may be at least about 3 days. The weight of the lake water may compact the mixture into the lake bed soil subsurface. The lake bed may be scarified before or after adding the crop plant biomass microorganism-expressed enzyme composition. Chains may be dragged across the lake bed. Further, analysis of the soil composition of the lake bed may be carried out. A target soil composition for the lake bed may, for example, be selected that includes cohesive colloidal fines passing a 200 mesh screen at a concentration within a range of between about 25% by weight and about 30% by weight of the soil. If a concentration of cohesive fines in the lake bed is deficient, then cohesive fines such as bentonite clay may be dispersed over the lake bed. It is understood that the above discussion regarding lake beds is applicable to other types of water bodies confined by a soil subsurface, such as containment structures, canals, landfills, reservoirs, lake beds, drainage areas, mine leach ponds, water ducts, and levees.

Mixing the crop plant biomass microorganism-expressed enzyme composition with the soil to be stabilized may be carried out for example, as needed, by blading the soil into a windrow with road building equipment. The windrow may then be bladed from side to side across the roadway over the subsurface. A grader may also be utilized. In another example, the soil to be stabilized may be removed from the subsurface, mixed elsewhere with the crop plant biomass microorganism-expressed enzyme composition, and then deposited onto the subsurface. A moisture content of the soil to be stabilized may be determined, and a suitable amount of water may be mixed with the soil. A hydrometer may be utilized, for example, to determine and monitor the moisture concentration of the soil to be stabilized. An optimum water concentration in the soil within a range of between about 15% and about 20% by weight may, for example, be selected. A water concentration in the soil that is within a range of between about 2% by weight and about 3% by weight below such an optimum water concentration may then for example be selected as a target water concentration in carrying out step 220. Such a water concentration may be adequate for mixing, while allowing a margin of error to avoid excessive water addition that might necessitate drying the soil. A rough determination of an appropriate water concentration in the soil may be made by attempting to make a small, cohesive ball of soil between one's fingers. When a soil to be stabilized has a water concentration that is too high, the soil may be dried, as an example, by successively blading the soil in windrows to facilitate water evaporation.

Step 220 may be carried out, for example, at a time when the daytime ambient temperature reaches a high of at least about 50 degrees Fahrenheit, and when the nighttime ambient temperature reaches a low that is above about 32 degrees Fahrenheit.

A crop plant biomass microorganism-expressed enzyme composition may be applied to a dusty soil surface for dust control at a dilution rate, for example, of about 10,000 gallons water to 1 gallon of the concentrated crop plant biomass microorganism-expressed enzyme composition.

In step 225, the mixture including a crop plant biomass microorganism-expressed enzyme composition and the soil to be stabilized, may be allowed to sit for awhile before shaping the soil in step 235. Step 225 may facilitate absorption of the crop plant biomass microorganism-expressed enzyme composition into the soil. For example, step 225 may include leaving the mixture overnight in a windrow.

At step 230, the water concentration of the mixture including a crop plant biomass microorganism-expressed enzyme composition and the soil to be stabilized may be determined and potentially adjusted. In an example where the mixture is allowed to sit overnight in step 225, step 230 may be carried out to ensure that the water concentration of the mixture remains sufficient. Hydrometer monitoring may be utilized, and a selected amount of additional water may be added to and mixed with the soil. Such additional water may include a crop plant biomass microorganism -expressed enzyme composition. A suitable dilution factor for a concentrated crop plant biomass microorganism-expressed enzyme composition may be, for example, about 1 gallon of concentrate in about 10,000 gallons of water, although other concentrations may be utilized. After applying the enzyme composition to the soil, as necessary, additional water may be applied to bring the moisture content closer to the amount needed for proper compaction.

At step 235, the mixture including a crop plant biomass microorganism-expressed enzyme composition and the soil to be stabilized is shaped into a selected structure. For example, the soil to be stabilized may be deposited onto the subsurface, earlier discussed, in one or more lifts. Each such lift may, as an example, have a thickness within a range of between about 2 inches and about 6 inches, or within a range of between about 2 inches and about 3 inches. Lifts within such thicknesses may be high enough so that compaction of the selected structure may be done in a minimized series of passes, while not being too high for the selected compaction equipment to be effective. Lifts having a thickness of less them about 2 inches and greater than about 6 inches may also be utilized. The subsurface may be moistened with a crop plant biomass microorganism -expressed enzyme composition diluted in water before depositing a first lift. A dilution of 1 gallon of concentrated crop plant biomass microorganism-expressed enzyme composition in 10,000 gallons of water may be utilized, among other concentrations. A surface on which any successive lifts are then deposited may be similarly moistened before depositing each lift, as needed. A total accumulation of up to about 24 inches of soil lifts or more may be deposited on a subsurface. In addition to forming selected soil lifts, it is understood that shaping of a selected structure may include providing for proper drainage including crowning and side drainage. In a further example, step 235 may include causing the mixture to be shaped into a selected structure including a brick, block, board, tile, or paver.

In step 240, the selected structure is compacted. Where multiple lifts are to be deposited, each successive lift may be compacted before deposition of the next lift. The soil to be stabilized may be compacted utilizing static weight, kneading, or vibration, among other known methods of compaction. Static weight, kneading and vibration may, for example, be applied to compact a soil lift utilizing a drum roller, a sheeps foot roller, and a vibrating roller, respectively. The vibration in a vibrating roller may be turned off after two compaction passes, to avoid fracturing previously compacted soil lifts. Compaction of soil lifts may be determined and monitored utilizing, for example, the American Association of State Highway and Transportation Officials ("AASHTO") Standard Method T 99-01 "Moisture-Density Relations of Soils Using a 5.5-Pound Rammer and a 12-Inch Drop", the entirety of which is incorporated into this application by reference. Each lift may be compacted to at least about 95% as determined by AASHTO Method T-99-01, or to other compaction percentages in practice. Compaction of soil lifts may also be determined and monitored, as an example, utilizing ASTM International Standard D698-00ae1 "Standard Test Methods for Laboratory Compaction Characteristics of Soil Using Standard Effort", the entirety of which is incorporated into this application by reference. As an example, the compaction density may be about 98 to 102% of optimum density, as measured using ASTM-D-698. In addition, soil density may be determined and monitored, as an example, utilizing a nuclear moisture-density meter. Compaction densities of up to 100-105 percent may, for example, be reached. Compaction may be achieved and then the surface may be worked to a smooth finish with a rubber tire or smooth steel-wheeled roller, or other smoothing devices.

The selected structure may be a construction article 100. Step 240 may then be carried out by applying compressive pressure to a mixture including soil and a crop plant biomass microorganism-expressed enzyme composition confined to a selected article shape such as that of a brick, block, board, tile, paver, or other construction article.

Final shaping of the selected structure may be carried out at step 245. Following completion of deposition and compaction of soil lifts, parts of such lifts may be removed and pushed aside, leaving behind a compacted soil structure having a selected shape. As an example, a new lake bed may be constructed by forming a perimeter berm in a series of compacted lifts having roughly the selected lake bed dimensions, and then blading the compacted soil structure to selected elevations. Where a liner is installed, the top 10 to 12 inches of a soil base may, for example, be subjected to the method 200 to provide a stable base for most lake bed liners.

In another example, at step 250 final compaction of the selected soil structure may be carried out. In an example, step 250 may be utilized following step 245 to re-compact surface soil disturbed by the final shaping.

At step 255, the selected soil structure may be allowed to cure undisturbed. In an example, curing may be completed in warm ambient temperatures over a period of about 3 days. As an example, the selected structure may become cured without application of heat, provided that a daytime high temperature of at least about 50 degrees Fahrenheit is reached and provided that a nighttime low temperature measured at the soil surface is above about 32 degrees Fahrenheit, in most instances.

In step 260, a wear surface may be applied over the stabilized soil. As an example, high speed road traffic may merit protection of the stabilized soil by application of a protective layer. In examples, a chip seal or an asphalt layer may be applied. A 3 to 5 day curing period for the soil stabilized by the method 200 may be allowed before such application.

The stabilized soil surface may be moistened before application of the protective layer by a diluted crop plant biomass microorganism-expressed enzyme composition in the same manner as earlier discussed. Further, the stabilized soil surface may be dressed to remove surface bumps and pits, so that a smooth protective layer may be applied. The method 200 may then end at step 265.

The soil stabilized by the method 200 may, as examples, have increased resilient modulus and increased shear strength. As an example, the resilient modulus of a soil to be stabilized may be relatively increased by a factor within a range of between about 30% and about 100%. As another example, the resilient modulus of a soil to be stabilized may be relatively increased by a factor within an average range of between about 69% and about 77%. In another example, the shear strength of a soil to be stabilized may be relatively increased by an average factor within a range of between about 31% and about 39%. Development of maximum resilient modulus may be delayed for a period of time, in certain instances up to about 5 months after completion of the method 200. Development of maximum shear strength may be delayed for a period of time, in certain instances up to about 4 months after completion of the method 200. The resilient modulus of soil may be determined by utilizing the test procedures in National Cooperative Highway Research Program Project 1-28A, "Laboratory Determination of Resilient Modulus for Flexible Pavement Design", the entirety of which is incorporated in this application by reference. Further, the resilient modulus of soil may further be determined by utilizing the test procedures in Strategic Highway Research Program ("SHRP") Protocol 46 "Resilient Modulus of Unbound Granular Base/Subbase Materials and Subgrade Soils", as modified in SHRP-P-693, "Type II Unbound Cohesive Subgrade Soil Synthetic Reference Sample Program", Washington, D.C. 1994, the entirety of which is incorporated in this application by reference.

The soil stabilized by the method 200 may exhibit decreased surface water permeability, increased structural integrity, increased surface wear resistance, increased load bearing capacity, and increased resistance to surface deterioration due to weather exposure including frost heaving.

Soil stabilization by the example method 200 may be utilized for dust control, trails, roads, parking lots, slope stabilization including railway embankments, air strips, pipe bedding, and soil surfaces intended to receive continuous water exposure including containment structures, canals, landfills, reservoirs, lake beds, drainage areas, mine leach ponds, water ducts, and levees, in addition to other applications. In slope stabilization applications, as an example, no vegetation such as straw and no matting may need to be applied.

The foregoing description of an implementation has been presented for purposes of illustration and description. It is not exhaustive and does not limit the claimed inventions to the precise forms disclosed. Modifications and variations are possible in light of the above description or may be acquired from practicing the invention. Note also that the implementation may vary. In addition to the article and method features described in this document, those skilled in the art will recognize that other features may be included or offered in connection with the articles and methods and should be viewed as within the scope of this invention. For example, the articles may be formed into any selected shape for which a composition including soil may have utility. As another example, the soil stabilization methods may be applied to any soil surface that may benefit from a hardening and a reduction in water permeability. The claims and their equivalents define the scope of the invention.

What is claimed is:

1. A construction article comprising at least one article of construction formed from a compacted mixture including clay-containing soil and a ureolytic enzyme composition.

2. The construction article of claim 1, in which the enzyme composition includes an active ureolytic enzyme.

3. The construction article of claim 1, in which the mixture includes a nitrate ion source.

4. The construction article of claim 1, in which the mixture has a pH within a range of between about 7 and about 8.

5. The construction article of claim 1, in which the enzyme composition is biodegradable.

6. The construction article of claim 1, in which the enzyme composition is edible.

7. The construction article of claim 1, in which the soil includes cohesive colloidal fines passing a 200 mesh screen at a concentration within a range of between about 8% by weight and about 30% by weight of the soil.

8. The construction article of claim 1, in which the mixture includes less than about 10% by weight of cellulosic material.

9. The construction article of claim 1, in which the article is selected from a group consisting of a brick, block, board, tile, and paver.

10. A method of stabilizing soil, comprising:
    mixing together clay-containing soil, water and a ureolytic enzyme composition to form a mixture;
    causing the mixture to be shaped into a selected structure; and
    causing the structure to be compacted.

11. The method of claim 10, including mixing together soil, water and the ureolytic enzyme composition that includes an active ureolytic enzyme.

12. The method of claim 10, including mixing together soil, water and the ureolytic enzyme composition that includes an enzyme expressed by a ureolytic microorganism.

13. The method of claim 10, including mixing together soil, water, the ureolytic enzyme composition, and a nitrate ion source.

14. The method of claim 10, including mixing together soil, water and the ureolytic enzyme composition that has a pH within a range of between about 7 and about 8.

15. The method of claim 10, including mixing together soil, water and the ureolytic enzyme composition that is biodegradable.

16. The method of claim 10, including mixing together soil, water and the ureolytic enzyme composition that is edible.

17. The method of claim 10, including selecting clay-containing soil including cohesive colloidal fines passing a 200 mesh screen at a concentration within a range of between about 8% by weight and about 30% by weight of the soil.

18. The method of claim 10, including selecting such a mixture including less than about 10% by weight of cellulosic material.

19. The method of claim 10, including selecting such a mixture including a water concentration within a range of between about 15% by weight and about 20% by weight of the mixture.

20. The method of claim 10, in which causing such a mixture to be shaped into a selected structure includes forming at least one lift having a thickness within a range of between about 2 inches and about 6 inches.

21. The method of claim 10, in which causing such a mixture to be shaped into a selected structure includes forming an article selected from a group consisting of a brick, block, board, tile, and paver.

22. A method of stabilizing soil, comprising:

mixing together soil, water and a crop plant biomass microorganism-expressed enzyme composition to form a mixture;

forming the mixture over a soil subsurface moistened by a solution including water and the crop plant biomass microorganism-expressed enzyme composition; and compacting the mixture.

23. The method of claim 22, in which the mixing step includes spraying the solution over the soil.

24. The method of claim 22, further comprising removing the soil to be mixed from the soil subsurface prior to the mixing step.

25. The method of claim 24, in which the forming step includes spreading the mixture over the soil subsurface from which the soil to be mixed was previously removed.

26. The method of claim 22, further comprising scarifying the surface of the soil to a selected depth prior to the mixing step, where the soil subsurface is located below the depth of the scarified soil.

27. The method of claim 22, further comprising applying a wear surface on the compacted mixture.

28. The method of claim 22, in which the enzyme composition includes a ureolytic enzyme.

29. A method of stabilizing soil, comprising:

dispersing a crop plant biomass microorganism-expressed enzyme composition in a water body confined by a soil subsurface;

allowing the enzyme composition in the water body to form a mixture on the soil subsurface, where the mixture includes soil, water, and the enzyme composition; and allowing the water body to compact the mixture on the soil subsurface.

30. The method of claim 29, further comprising scarifying the subsurface of the water body.

31. The method of clam 29, where the enzyme composition includes a ureolytic enzyme.

* * * * *